United States Patent
Catinat et al.

(10) Patent No.: US 6,429,322 B1
(45) Date of Patent: Aug. 6, 2002

(54) METHOD FOR MAKING AN OXIRANE

(75) Inventors: Jean-Pierre Catinat, Waudrez; Michel Strebelle, Brussels, both of (BE)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 09/646,788

(22) PCT Filed: Sep. 20, 1999

(86) PCT No.: PCT/EP99/01955

§ 371 (c)(1),
(2), (4) Date: Sep. 22, 2000

(87) PCT Pub. No.: WO99/48882

PCT Pub. Date: Sep. 30, 1999

(30) Foreign Application Priority Data

Mar. 24, 1998 (BE) ............................................ 09800231

(51) Int. Cl.⁷ ............................................ C07D 301/12
(52) U.S. Cl. ........................................ 549/531; 549/524
(58) Field of Search ................................... 549/531, 524

(56) References Cited

FOREIGN PATENT DOCUMENTS

| EP | 712852 | * | 5/1996 |
| EP | 795537 | * | 9/1997 |

OTHER PUBLICATIONS

Clerici et al, Journal of Catalyst, 140, pp. 71–83, 1993.*

* cited by examiner

*Primary Examiner*—Ba K. Trinh
(74) *Attorney, Agent, or Firm*—Larson & Taylor PLC

(57) ABSTRACT

Process for manufacturing an epoxide by reaction between an olefin and a peroxide compound in the presence of a zeolite-based catalyst and in the presence of a solvent, in which the pH of the reaction medium comprising the olefin, the peroxide compound, the catalyst, the epoxide formed and the solvent is from 4.8 to 6.5.

10 Claims, No Drawings

METHOD FOR MAKING AN OXIRANE

The invention relates to a process for manufacturing an epoxide by reaction between an olefin and a peroxide compound in the presence of a zeolite-based catalyst. The invention relates more particularly to a process for manufacturing 1,2-epoxypropane (or propylene oxide) by reaction between propylene and hydrogen peroxide.

It is known practice to manufacture propylene oxide by epoxidation of propylene using hydrogen peroxide and in the presence of a catalyst of the type TS-1, as described, for example, in patent application EP 0 230 949. This known process has the drawback of leading, under certain conditions, to selectivities and/or degrees of conversion of hydrogen peroxide which are too low.

The invention is directed towards overcoming this drawback by providing a process for manufacturing an epoxide which is of high selectivity and/or high degree of conversion.

The invention consequently relates to a process for manufacturing an epoxide by reaction between an olefin and a peroxide compound in the presence of a zeolite-based catalyst and a solvent, in which the pH of the reaction medium comprising the olefin, the peroxide compound, the catalyst, the epoxide formed and the solvent is from 4.8 to 6.5.

One of the essential characteristics of the invention lies in the pH. The reason for this is that it has been observed that the acidity of the catalyst plays an important role in obtaining a good compromise between the selectivity and the degree of conversion of the peroxide compound. In general, too high an acidity leads to poor results. However, the acidity of the catalyst is difficult to control at the level of the catalyst itself since products which affect the acidity, i.e. by-products formed during the epoxidation and acids entrained by the recycling of the catalyst and the solvent and by the unconverted olefin, are readily adsorbed onto the surface of the catalyst. In addition, these products are not easy to remove during the regeneration of the catalyst. It has now been found that the problem of acidity of the catalyst can be solved by maintaining the pH of the epoxidation reaction medium at a value of at least 4.8, preferably at least 5. The pH should not exceed a value of 6.5, preferably 6. This in fact makes it possible to obtain a good compromise between the selectivity and the degree of conversion of the peroxide compound. Good results are obtained when the pH of the reaction medium is maintained at from 4.8 to 6.5, preferably from 5 to 6.

In the process according to the invention, the pH of the reaction medium can be controlled by addition of a base. This base can be chosen from water-soluble bases. These can be strong bases. As examples of strong bases, mention may be made of NaOH, KOH or quaternary ammonium hydroxides of general formula $NR_4^+OH^-$ (R=alkyl). They can also be weak bases. The weak bases can be inorganic. As examples of weak inorganic bases, mention may be made of $NH_4OH$, $Na_2CO_3$, $NaHCO_3$, $Na_2HPO_4$, $K_2CO_3$, $Li_2CO_3$, $KHCO_3$, $LiHCO_3$ and $K_2HPO_4$. The weak bases can also be organic. Weak organic bases which may be suitable are the alkali metal or alkaline-earth metal salts of carboxylic acids preferably containing from 1 to 10 carbon atoms. Weak bases give good results. Weak organic bases are preferred. Sodium acetate is particularly suitable.

The peroxide compounds which can be used in the process according to the invention are peroxide compounds containing active oxygen which are capable of carrying out an epoxidation. Hydrogen peroxide and peroxide compounds which can produce hydrogen peroxide under the epoxidation reaction conditions are suitable for use. Hydrogen peroxide is preferred.

In the process according to the invention, the peroxide compound is generally used in an amount of at least 1 mol per kg of reaction medium, in particular at least 1.5 mol per kg of reaction medium. The amount of peroxide compound is generally less than 10 mol per kg of reaction medium; it is usually less than or equal to 5 mol per kg of reaction medium, in particular less than or equal to 3 mol per kg of reaction medium.

In the process according to the invention, the peroxide compound is advantageously used in the form of an aqueous solution. In general, the aqueous solution contains at least 10% by weight of peroxide compound, in particular at least 20% by weight. It usually contains not more than 70% by weight of peroxide compound, in particular 50% by weight.

In the process according to the invention, the olefin reacts with the peroxide compound in the presence of the catalyst and the solvent at a temperature which is generally at least 0° C., in particular at least 20° C. The temperature is generally less than 150° C.; it is usually less than or equal to 70° C., in particular less than or equal to 40° C.

In the process according to the invention, the reaction between the olefin and the peroxide compound can take place at atmospheric pressure. It can also take place under pressure. Generally, this pressure does not exceed 40 bar. A pressure of 20 bar is suitable in practice.

The catalysts used in the process according to the invention contain a zeolite, i.e. a solid containing silica which has a microporous crystalline structure. The zeolite is advantageously free of aluminium. It preferably contains titanium.

The zeolite which can be used in the process according to the invention can have a crystalline structure of ZSM-5, ZSM-11, MCM-41 type or of beta-zeolite type. Zeolites of ZSM-5 type are suitable for use. Those with an infrared absorption band at about 950–960 $cm^{-1}$ are preferred.

The zeolites which are particularly suitable are the titanium silicalites. Those corresponding to the formula $xTiO_2$ $(1-x)SiO_2$ in which x is from 0.0001 to 0.5, preferably from 0.001 to 0.05, give good performance. Materials of this type, known under the name TS-1 and having a crystalline structure of ZSM-5 type, give particularly favourable results.

The epoxide which can be prepared by the process according to the invention is an organic compound comprising a group corresponding to the general formula:

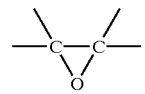

The epoxide generally contains from 2 to 20 carbon atoms, preferably from 3 to 10 carbon atoms. An epoxide which can be prepared advantageously by the process according to the invention is 1,2-epoxypropane.

The olefins which are suitable in the process according to the invention contain from 3 to 10 carbon atoms. Propylene is preferred.

The solvent used in the process according to the invention is generally substantially water-miscible. Solvents which give good results are aliphatic organic derivatives containing from 1 to 4 carbon atoms. Methanol may be mentioned by way of example.

The molar ratio between the amount of olefin used and the amount of peroxide compound is generally greater than or equal to 1, in particular greater than or equal to 1.5. This molar ratio is usually less than or equal to 20, in particular less than or equal to 10.

During continuous tests, the molar ratio between the amount of olefin used and the amount of solvent is generally greater than or equal to 0.1, preferably greater than or equal to 0.5. This molar ratio is usually less than or equal to 50, preferably less than or equal to 10.

The process according to the invention can be carried out continuously. As a variant, it can be carried out in a batchwise manner.

EXAMPLE

Propylene oxide was manufactured by reaction between propylene and hydrogen peroxide in the presence of a catalyst TS-1 and in the presence of methanol. In Example 1 given for comparative purposes, the pH of the reaction medium is maintained at a value of less than 4.8. In Examples 2 to 4 in accordance with the invention, the pH of the reaction medium is maintained at a pH of 4.8 to 6.5 by addition of sodium acetate.

The results are collated in Table 1 below. The tests were carried out in a batchwise manner at a temperature of 35° C., with a flow rate of propylene of 10 mol/h for 0.6 mol of hydrogen peroxide added in the form of an aqueous solution containing 35% by weight of hydrogen peroxide. The amount of methanol used was 14.4 mol/mol $H_2O_2$ (360 ml). The catalyst was used in an amount of 6.8 g.

In the examples which follow, the rate of conversion of the hydrogen peroxide is expressed by the rate constant k, which is first order, corresponding to the relationship: rate= kx (concentration of $H_2O_2$). The selectivity is given by the ratio between the amount of epoxide obtained divided by the sum of all of the products formed.

TABLE 1

| Example | pH  | Selectivity | k (min$^{-1}$) |
|---------|-----|-------------|----------------|
| 1       | 4.0 | 84.0        | 59             |
| 2       | 5.5 | 90.7        | 26             |
| 3       | 6.0 | 97.4        | 15             |
| 4       | 6.3 | 98.1        | 1.6            |

What is claimed is:

1. A process for manufacturing 1,2, epoxypropane by reaction between propylene and a peroxide compound in the presence of zeolite-based catalyst and in the presence of a solvent, wherein the pH of the reaction medium comprising the propylene, the peroxide compound, the catalyst, the 1,2, epoxypropane formed and the solvent is from 4.8 to 6.

2. The process according to claim 1, wherein the pH of the reaction medium is from 5 to 6.

3. The process according to claim 1, in which the peroxide compound is used in an amount of from 1 to 10 mol, preferably from 1.5 to 5 mol, per kg of reaction medium.

4. The process according to claim 1, wherein the peroxide compound is used in the form of an aqueous solution containing from 10 to 70% of peroxide compound, preferably from 20 to 50%.

5. The process according to claim 1, wherein the reaction is carried out at a temperature of from 0 to 150° C., generally from 0 to 70° C., preferably from 20 to 40° C.

6. The process according to claim 1, wherein the pH of the reaction medium is maintained in the zone form 4.8 to 6 by the addition of a base.

7. The process according to claim 6, wherein the base is chosen from weak bases.

8. The process according to claim 7, wherein the base is sodium acetate.

9. The process according to claim 1, wherein the zeolite is titanium silicalite, preferably of TS-1 type with a crystalline structure of ZSM-5 type.

10. The process according to claim 1, wherein the peroxide compound is hydrogen peroxide and the solvent is methanol.

* * * * *